United States Patent [19]  [11] 4,285,939
Machida et al.  [45] Aug. 25, 1981

[54] CEPHALOSPORIN DERIVATIVES, AND ANTIBACTERIAL DRUGS CONTAINING THE DERIVATIVES

[75] Inventors: Yoshimasa Machida, Wako; Isao Saito, Chofu; Motosuke Yamanaka, Urawa; Seiichiro Nomoto, Tokyo; Shigeto Negi, Kodaira; Kyosuke Kitoh, Kawague; Kanemasa Katsu, Chofu; Yukio Ohya, Koganei; Takeshi Suzuki; Kyoko Koizumi, both of Abiko, all of Japan

[73] Assignee: Eisai Co., Ltd., Tokyo, Japan

[21] Appl. No.: 137,753

[22] Filed: Apr. 7, 1980

[30] Foreign Application Priority Data

Apr. 9, 1979 [JP] Japan ................................. 54-42023

[51] Int. Cl.³ ........................................... C07D 501/20
[52] U.S. Cl. ..................................... 424/246; 544/28
[58] Field of Search ...................... 544/30, 28, 26, 27; 424/270, 246, 271

[56] References Cited

U.S. PATENT DOCUMENTS

4,015,000  3/1977  Kocsis et al. ......................... 544/260
4,101,661  7/1978  Kaltenbronn et al. ................ 544/26

Primary Examiner—Nicholas S. Rizzo
Attorney, Agent, or Firm—Wenderoth, Lind & Ponack

[57] ABSTRACT

New cephalosporin derivatives represented by the general formula:

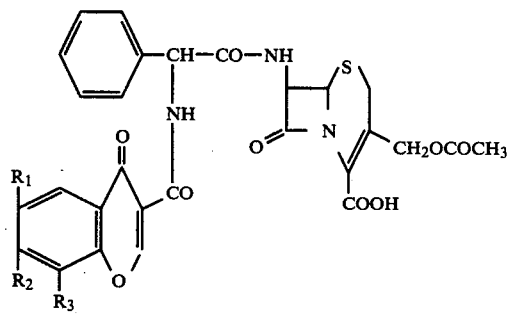

wherein $R_1$, $R_2$, and $R_3$ each represents hydroxy, acyloxy, and hydrogen provided that two or three of $R_1$, $R_2$, and $R_3$ are not hydrogen at the same time, and their salts, and processes for the preparation thereof. The cephalosporin derivatives of the present invention are useful as antibacterial drugs.

6 Claims, No Drawings

CEPHALOSPORIN DERIVATIVES, AND ANTIBACTERIAL DRUGS CONTAINING THE DERIVATIVES

This invention relates to novel cephalosporin derivatives as represented by the general formula (I):

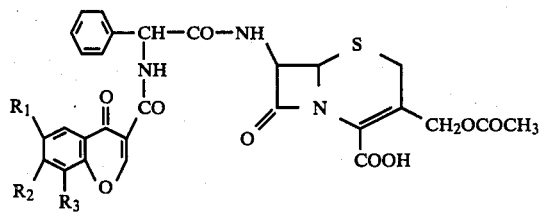

wherein $R_1$, $R_2$ and $R_3$ each represents hydroxy, acyloxy, or hydrogen provided that two or three of $R_1$, $R_2$, and $R_3$ are not hydrogen at the same time, their non-toxic salts, processes for the preparation thereof and antibacterial drugs comprising them.

The compound represented by the formula (II):

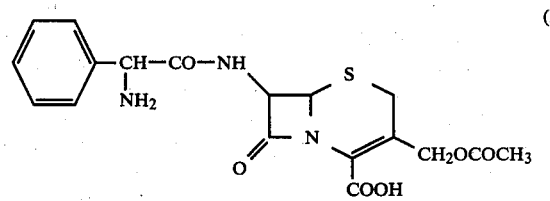

is known as cephaloglycin and is disclosed in Belgian Pat. No. 635,137 (1964).

The object of this invention is to provide novel antibacterial drugs which are produced by acylating the amino group in the phenylglycine moiety of cephaloglycin (II).

Examples of the said acyloxy groups in the compounds (I) of this invention are acetoxy, propionyloxy, etc. Illustrative of non-toxic salts of the compounds (I) of this invention are sodium salts, potassium salts, procaine salts, etc.

The compounds of this invention are prepared by the following processes.

The compound of the general formula (I) of this invention can be prepared by reacting the compound of the formula (II) or its salt or hydrate with a compound represented by the general formula (III):

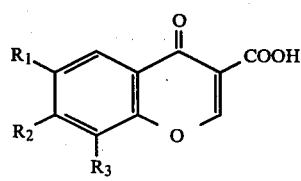

wherein $R_1$, $R_2$, and $R_3$ are the same as set forth above, or its reactive derivative thereof.

When the carboxylic acid of the general formula (III) is used as it is in the said reaction, it is preferable to effect the reaction in the presence of a condensation reagent such as N,N'-dicyclohexylcarbodiimide, N,N'-diethylcarbodiimide, N,N'-dipropylcarbodiimide, N-cyclohexyl-N'-morpholinoethylcarbodiimide, trialkyl phosphite, ethyl polyphosphate, phosphorus oxychloride, oxalyl chloride, etc. The examples of the reactive derivatives of the carboxylic acids of the general formula (III) are, for example, an acid halide such as acid chloride, acid bromide, etc; a symmetric anhydride; a mixed anhydride derived from chlorocarbonate ester, trimethylacetic acid, thioacetic acid, diphenylacetic acid, etc; a reactive ester derived from 2-mercaptopyridine, cyanomethanol, p-nitrophenol, 2,4-dinitrophenol, pentachlorophenol, etc; a reactive acid amide such as N-acylsaccharin, N-acylphthalimide, etc.

The reactions between the compounds of the formula (II) and the compounds of the general formula (III) can be carried out in an inert solvent at a temperature range of $-50°$ to $50°$ C., preferably at temperatures between $-20°$ and $30°$ C. in the presence or absence of a basic or silylating reagent.

Illustrative of the said inert solvents are acetone, tetrahydrofuran, dimethylacetamide, dioxane, dichloromethane, chloroform, benzene, toluene and ethyl acetate, and mixtures thereof.

Illustrative of the said basic reagents are, for example, alkali hydroxides such as potassium hydroxide, sodium hydroxide, etc; alkali hydrogen carbonates such as potassium hydrogen carbonate, sodium hydrogen carbonate, etc; and amines such as triethylamine, pyridine, N-methylmorpholine, etc.

Illustrative of the said silylating reagents are, for example, N,O-bis(trimethylsilyl)acetamide, hexamethyldisilazane, etc.

The chromone carboxylic acid (III) used as the starting material in this invention can be generally obtained by oxidizing an aldehyde of the general formula (IV):

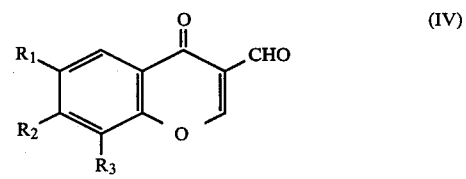

wherein $R_1$, $R_2$, and $R_3$ are the same as set forth above, except that they do not represent hydroxy groups, with Jones reagent (see Reagents for Organic Synthesis, Vol. 1, p 142).

The chromone carboxylic acids wherein any of $R_1$, $R_2$ and $R_3$ are hydroxy groups can be obtained by oxidizing the aldehydes (IV) which contain acyloxy groups in place of the hydroxy groups according to the above-described process, followed by hydrolozing the said acyloxy groups.

The chromone carboxylic acid halides of the compound (III) can be obtained by reacting the acid of the formula (III) with a halogenating reagent such as phosphorus pentachloride, thionyl chloride, etc.

The aldehyde of the formula (IV) can be prepared by the conventional processes, for example, the processes described in Tetrahedron 30, 3553 (1974).

Alternatively, the compound of the general formula (I), wherein, $R_1$, $R_2$, and $R_3$ each is hydroxy or hydrogen provided that two or three of $R_1$, $R_2$, and $R_3$ are not hydrogen at the same time, of this invention can be prepared by hydrolyzing the acyloxy moieties of the compound (I) wherein $R_1$, $R_2$, and $R_3$ each is acyloxy or hydrogen provided that two or three of $R_1$, $R_2$, and $R_3$ are not hydrogen at the same time.

The alkali hydrogen carbonates such as sodium hydrogen carbonate, potassium hydrogen carbonate, etc. may be used for the purpose of effecting the said hydrolysis.

Illustrative of specified compounds of this invention are the following compounds and their sodium salts.

7β-[D-2-(6,7-Diacetoxychromone-3-carboxamido)-2-phenylacetamido]-3-acetoxymethyl-3-cephem-4-carboxylic acid.

7β-[D-2-(6,7-Dihydroxychromone-3-carboxamido)-2-phenylacetamido]-3-acetoxymethyl-3-cephem-4-carboxylic acid.

7β-[D-2-(7,8-Diacetoxychromone-3-carboxamido)-2-phenylacetamido]-3-acetoxymethyl-3-cephem-4-carboxylic acid.

7β-[D-2-(7,8-Dihydroxychromone-3-carboxamido)-2-phenylacetamido]-3-acetoxymethyl-3-cephem-4-carboxylic acid.

7β-[D-2-(6,8-Diacetoxychromone-3-carboxamido)-2-phenylacetamido]-3-acetoxymethyl-3-cephem-4-carboxylic acid.

7β-[D-2-(6,8-Dihydroxychromone-3-carboxamido)-2-phenylacetamido]-3-acetoxymethyl-3-cephem-4-carboxylic acid.

7β-[D-2-(6,7,8-Triacetoxychromone-3-carboxamido)-2-phenylacetamido]-3-acetoxymethyl-3-cephem-4-carboxylic acid.

7β-[D-2-(6,7,8-Trihydroxychromone-3-carboxamido)-2-phenylacetamido]-3-acetoxymethyl-3-cephem-4-carboxylic acid.

The cephalosporin derivatives of this invention have excellent antibacterial activities and are effective not only against the Gram-positive bacteria, but also against the Gram-negative bacteria. The said cephalosporin derivatives are characterized in that they exhibit remarkable effect, particularly, against *Pseudomonas aeruginosa* which causes difficulty curable infections.

Moreover, it has been confirmed that the compounds of this invention show low toxicity in the toxicity test. For example, the acute toxicity values [$LD_{50}$ (mouse, oral)] for the following compounds were over 5 g/kg:

Sodium salt of 7β-[D-2-(6,7-dihydroxychromone-3-carboxamido)-2-phenylacetamido]-3-acetoxymethyl-3-cephem-4-carboxylic acid and Sodium salt of 7β-[D-2-(6,7-dihydroxychromone-3-carboxamido)-2-phenylacetamido]-3-acetoxymethyl-3-cephem-4-carboxylic acid.

Dosage of the compound of this invention as anti-bacterial drug may range generally from about 2 to 300 mg/kg/day, and preferably from 10 to 100 mg/kg/day. The compounds of this invention can be administered orally or parenterally.

Pharmaceutical preparations containing the compounds of this invention can be produced by any conventional preparation processes. Therefore, this invention includes preparation compositions containing at least one of the present compounds suitable as the medicine for human. Such compositions are provided by conventional methods with any required pharmaceutical carriers or diluents.

Tablets and capsules for oral administration may be in unit dose presentation form, and may contain conventional excipients such as binding agents, syrup, gum arabic, gelatine, sorbitol, tragacanth or polyvinylpyrrolidone; diluents, for example, lactose, cornstarch, calcium phosphate, sorbitol, or glycine; lubricants, for example, magnesium stearate, talc, polyethylene glycol, or silica; disintegrants, for example, potato starch, or acceptable wetting agents, for example sodium lauryl sulfate.

The said tablet may be subjected to coating by a process well known in the art.

Liquid preparations for oral administration may be in the form of aqueous or oily emulsion, solution, syrup, elixir, etc.

Alternatively, they may be dry products which can be redissolved in water or any suitable vehicle before administration.

Such liquid preparations may contain conventional additive(s), for example, a suspending agent such as sorbitol syrup, methylcellulose, glucose/sugar syrup, gelatine, hydroxyethylcellulose, carboxymethylcellulose, aluminum stearate gel and hydrogenated edible fat; an emulsifier such as lecithin, mono-oleic acid sorbitan and gum arabic, a non-aqueous vehicle such as almond oil, fractionated coconut oil, oily ester, propylene glycol and ethanol, an antiseptics such as methyl p-hydroxybenzoate, propyl p-hydroxybenzoate and sorbic acid.

The composition for injection is provided in an ampoule of unit dosage or in a vial with added antiseptics. The said composition may be in the form of suspension, solution, or emulsion in an oily or aqueous vehicle, and may contain formulating agents such as suspending agent, stabilizer and/or dispersant. On the other hand, the active ingredient may be powder which can be redissolved before administration in suitable vehicle, for example, sterile pyrogen-free water.

The following experiments and examples illustrate this invention, but are not to be construed as limiting the scope thereof.

EXPERIMENT 1

Preparation of chromone-3-carboxylic acids which are the intermediates of the compounds of this invention.

(A) 6,7-Diacetoxychromone-3-carboxylic acid 6,7-Diacetoxychromone-3-carboxyaldehyde (17.8 g) was dissolved in 1 liter of acetone. To this solution was added with stirring Jones reagent (32.8 ml) which had been previously prepared by dissolving chromic acid (133.6 g) in concentrated sulfuric acid (115 ml) diluted with water to a volume of 500 ml.

The reaction mixture was concentrated to 100 ml, and poured into water (900 ml). The precipitates (6.5 g) were collected by filtration, and recrystallized from ethyl acetate to obtain the desired compound (5.9 g).

(B) 6,7-Dihydroxychromone-3-carboxylic acid

To 6,7-diacetoxychromone-3-carboxylic acid (15.3 g) produced in (A) were added acetic acid (300 ml) and concentrated hydrochloric acid (100 ml), and the mixture was stirred for 20 minutes at about 70° C., then cooled. The precipitates were collected by filtration, and recrystallized from N,N-dimethylformamide-water to obtain the desired compound (8.9 g).

7,8-Diacetoxychromone-3-carboxylic acid and 7,8-dihydroxychromone-3-carboxylic acid were prepared by the processes according to (A) and (B), respectively.

The properties of the resulting compounds are shown in Table 1.

TABLE 1

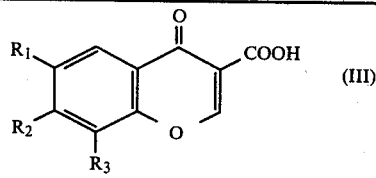

| No. | R₁ (III) | R₂ | R₃ | IR Spectrum (cm⁻¹, nujol) | Molecular Formula Melting point (°C.) | Elemental Analysis (%) Calculated: Found: C | H |
|---|---|---|---|---|---|---|---|
| 1 | HO— | HO— | H | 3370, 3300, 1730, 1635, 1620 | $C_{10}H_6O_6$ >300 | 54.06 54.05 | 2.72 2.60 |
| 2 | CH₃COO— | CH₃COO— | H | 1780, 1760, 1730, 1620 | $C_{14}H_{10}O_8$ 186–188 | 54.91 54.95 | 3.29 3.08 |
| 3 | H | HO— | HO— | 3380, 3275, 1725, 1620 | $C_{10}H_6O_6$ 265–270* | 54.06 53.65 | 2.72 2.53 |
| 4 | H | CH₃COO— | CH₃COO— | 1780, 1760, 1740, 1625 | $C_{14}H_{10}O_8$ 178–179 | 54.91 54.90 | 3.29 3.25 |

*decomposition

EXAMPLE 1

7β-[D-2-(6,7-Diacetoxychromone-3-carboxamido)-2-phenylacetamido]-3-acetoxymethyl-3-cephem-4-carboxylic acid and its sodium salt (a) 6,7-Diacetoxychromone-3-carbonyl chloride A mixture of 6,7-Diacetoxychromone-3-carboxylic acid (918 mg, 3 mmol), benzene (20 ml), thionyl chloride (260 μl, 3.6 mmol) and N,N-dimethylformamide (0.2 ml) was refluxed for 2 hours and the solvent was removed. Benzene (5 ml) was added and then evaporated. This was repeated twice to remove traces of thionyl chloride. The residual solid was collected to afford the desired compound.

IR spectrum (cm⁻¹, nujol): 1780, 1775, 1660, 1625.

(b) 7β-[D-2-(6,7-Diacetoxychromone-3-carboxamido)-2-phenylacetamido]-3-acetoxymethyl-3-cephem-4-carboxylic acid N,O-Bis(trimethylsilyl)acetamide (1.483 ml, 6 mmol) was added to a stirred suspension of cephaloglycin (811 mg, 2.0 mmol) in dichloromethane (16 ml) at 0° C. The mixture was stirred for 20 minutes at 0° C., to which was added dropwise a suspension of the acid chloride (2 mmol) described in (a) in dichloromethane (10 ml). The stirring was continued for 0.5 hour at 0° C. and for a further 5 hours at room temperature and the solvent was removed. The residue was taken up in ethyl acetate (250 ml), washed successively with 0.5 N hydrochloric acid (40 ml×2), water (40 ml×2) and saturated brine (40 ml×2) and dried (MgSO₄). After removal of the solvent, the residue was triturated with ethyl ether to afford the desired compound (920 mg, 66%).

Melting point: 170°–175° C. (decomposition).

| Elemental analysis: for $C_{32}H_{27}N_3O_{13}S$ | | | |
|---|---|---|---|
| | C | H | N |
| Calculated (%): | 55.41 | 3.92 | 6.06 |
| Found (%): | 54.38 | 3.86 | 5.05 |

IR spectrum (cm⁻¹, nujol): 1780, 1735, 1690, 1665, 1620.

(c) Sodium salt of the compound described in (b)

Sodium 2-ethylhexanoate (0.5 M solution in ethyl acetate, 2 ml) was added to a solution of the compound (694 mg, 1 mmol) described in (b) in a mixture of acetone (30 ml) and N,N-dimethylformamide (2 ml). Ethyl acetate-ethyl ether (1:1, 30 ml) followed by ethyl ether (50 ml) was added to the mixture and the precipitate formed was filtered off, washed with ethyl acetate-ethyl ether (1:1) and dried to afford the desired compound (306 mmg, 43%).

Melting point: 165°–180° C. (decomposition).

| Elemental analysis: for $C_{32}H_{26}N_3NaO_{13}S$ | | | |
|---|---|---|---|
| | C | H | N |
| Calculated (%): | 53.77 | 3.66 | 5.87 |
| Found (%): | 52.35 | 3.83 | 5.37 |

IR spectrum (cm⁻¹, nujol): 1785, 1770, 1742, 1670, 1605.

NMR spectrum (δ, DMSO-d₆): 2.00 (3H, s), 2.37 (3H, s), 2.38 (3H, s), 3.13 (1H, d, J=17 Hz), 3.43 (1H, d, J=17 Hz), 4.78 (1H, d, J=12 Hz), 4.94 (1H, d, J=4.5 Hz), 5.02 (1H, d, J=12 Hz),
5.61 (1H, dd, J=8 Hz, 4.5 Hz), 5.94 (1H, d, J=8 Hz) 7.25–7.7 (5H, m), 7.92 (1H, s), 8.12 (1H, s), 9.09 (1H, s), 9.49 (1H, d, J=8 Hz), 10.15 (1H, d, J=8 Hz).

EXAMPLE 2

7β-[D-2-(6,7-Dihydroxychromone-3-carboxamido)-2-phenylacetamido]-3-acetoxymethyl-3cephem-4-carboxylic acid and its sodium salt (a) 6,7-Dihydroxychromone-3-carbonyl chloride A mixture of 6,7-dihydroxychromone-3-carboxylic acid (9.0 g, 4 mmol) and thionyl chloride (150 ml) was refluxed for 45 minutes and the thionyl chloride was evaporated. After the addition of benzene, the mixture was evaporated again to dryness and the residue was triturated with n-hexane to afford the desired compound (9.1 g, 93.4%).

IR spectrum (cm⁻¹, nujol): 1780, 1765, 1645, 1625.

(b) 7β-[D-2-(6,7-Dihydroxychromone-3-carboxamido)-2-phenylacetamido]-3-acetoxymethyl-4-carboxylic acid N,O-Bis(trimethylsilyl)acetamide (44.8 g, 54.4 mml, 220 mmol) was added to a stirred suspension of cephaloglycin (16.2 g, 40 mmol) in dichloromethane (400 ml) at 2° C. The mixture was stirred for 2 hours at 2° C., to which was added the acid chloride (8.7 g, 36 mmol) described in (a) and the stirring was continued for 1.5 hours at 2° C. The reaction mixture was diluted with ethyl acetate (1 liter), washed successively with ice-cooled, saturated brine, an ice-cooled mixture of 0.5 N hydrochloric acid and saturated brine (4 times) and dried (MgSO$_4$). The solvent was evaporated and the residue was triturated with n-hexane to afford a crude product (8.25 g). A suspension of a portion (1.8 g) of the product in acetone (60 ml) was stirred at room temperature for 2 days and after removal of acetone, the residue was triturated with ethyl ether and washed with n-hexane to afford the desired compound (1.5 g; Yield allowing for the untreated crude product: 28.2%).

Melting point: 240°–255° C. (decomposition).

| Elemental analysis: for C$_{28}$H$_{23}$N$_3$O$_{11}$S | | | |
|---|---|---|---|
| | C | H | N |
| Calculated (%): | 55.17 | 3.80 | 6.89 |
| Found (%): | 50.37 | 3.68 | 5.41 |

IR spectrum (cm$^{-1}$, nujol): 1780, 1735, 1710, 1660, 1630.

NMR spectrum (δ, DMSO-d$_6$): 2.04 (3H, s), 3.40 (1H, d, J=18 Hz), 3.52 (1H, d, J=18 Hz), 4.70 (1H, d, J=12 Hz), 4.98 (1H, d, J=12 Hz), 5.03 (1H, d, J=5 Hz), 5.74 (1H, dd, J=8 Hz, 5 Hz), 5.87 (1H, d, J=8 Hz), 7.02 (1H, s), 7.20–7.52 (5H, m), 7.44 (1H, s), 8.88 (1H, s), 9.50 (1H, d, J=8 Hz), 10.42 (1H, d, J=8 Hz).

(c) Sodium salt of the compound described in (b)

Sodium 2-ethylhexanoate (0.5 M solution in ethyl acetate, 6.0 ml) was added dropwise to a solution of the compound (1.83 g, 3 mmol) described in (b) in a mixture of acetone (850 ml) and N,N-dimethylformamide (13 ml). The mixture was stirred for 20 minutes at room temperature, to which was added successively ethyl acetate-ethyl ether (1:1, 800 ml) and ether (200 ml). After stirring for 30 minutes at room temperature, the precipitate was filtered off, washed with ethyl acetate and dried to afford the desired compound (1.24 g, 65.4%).

Melting point: 185°–195° C. (decomposition).

| Elemental analysis: for C$_{28}$H$_{22}$N$_3$NaO$_{11}$S | | | |
|---|---|---|---|
| | C | H | N |
| Calculated (%): | 53.25 | 3.67 | 6.65 |
| Found (%): | 48.73 | 3.74 | 5.53 |

IR spectrum (cm$^{-1}$, nujol): 1765, 2740, 1660, 1630, 1610.

NMR spectrum (δ, DMSO-d$_6$): 2.01 (3H, s), 3.20 (1H, d, J=18 Hz), 3.42 (1H, d, J=18 Hz), 4.80 (1H, d, J=12 Hz), 4.94 (1H, d, J=5 Hz), 5.01 (1H, d, J=12 Hz), 5.59 (1H, br.s), 5.90 (1H, d, J=8 Hz), 6.80 (1H, s), 7.20–7.60 (5H, m), 7.29 (1H, s), 8.76 (1H, s), 9.43 (1H, br.s), 10.64 (1H, d, J=8 Hz).

EXAMPLE 3

7β-[D-2-(6,7-Dihydroxychromone-3-carboxamido)-2-phenylacetamido]-3-acetoxymethyl-3-cephem-4-carboxylic acid Sodium hydrogen carbonate (1 M solution in water, 0.698 μl) was added to a solution of the compound (200 mg, 0.279 mmol) described in Example 1-c) in water (160 ml). The mixture was allowed to stand at room temperature for 7 days, acidified to pH 2.0 and then extracted with ethyl acetate (50 ml×4). The organic layer was washed successively with water and saturated brine, dried (MgSO$_4$) and evaporated. Trituration of the residue with ethyl ether afforded the desired compound (51 mg, 30%). This compound was identical with the compound described in Example 2-b) in all respects [NMR, IR and thin layer chromatography (silica gel, Merck 5715, benzene/dioxane/acetic acid=4:1:1)].

EXAMPLE 4

7β-[D-2-(7,8-Diacetoxychromone-3-carboxamido)-2-phenylacetamido]-3-acetoxymethyl-3-cephem-4-carboxylic acid (a) 7,8-Diacetoxychromone-3-carbonyl chloride A mixture of 7,8-diacetoxy-3-carboxylic acid (9.5 g, 31 mmol), thionyl chloride (2.6 ml), N,N-dimethylformamide (0.1 ml) and benzene (300 ml) was refluxed for 1.5 hours. After the addition of thionyl chloride (2.6 ml) and N,N-dimethylformamide (0.1 ml), the mixture was refluxed for an additional hour and evaporated to dryness. The residue was triturated with n-hexane to afford the desired compound (9.3 g, 92.6%).

IR spectrum (cm$^{-1}$, nujol): 1780, 1770, 1670, 1620.

(b) 7β-[D-2-(7,8-Diacetoxychromone-3-carboxamido)-2-phenylacetamido]-3-acetoxymethyl-3-cephem-4-carboxylic acid N,O-Bis(trimethylsilyl)acetamide (1 M solution in dichloromethane, 5.0 ml) was added dropwise to a stirred suspension of cephaloglycin (405 mg, 10 mmol) in ethyl acetate (10 ml) at 0° C. The mixture was stirred for 1 hour at 0° C., to which was added the acid chloride (325 mg, 1.0 mmol) described in (a)., after stirring for 4 hours at 0° C., the reaction mixture was diluted with ethyl acetate (300 ml), washed successively with water (40 ml), 0.5 N hydrochloric acid (40 ml×2), water (40 ml×2) and saturated brine (40 ml×2) and dried (MgSO$_4$).

Removal of the solvent afforded pale yellow crystals (402 mg). A portion (108 mg) of the crystals was purified by preparative thin layer chromatography on silica gel (developing solvent: chloroform/methanol/formic acid=90:10:4) to give the desired compound (24 mg, yield allowing for the untreated crude product: 14.0%).

Melting point: 150°–160° C. (decomposition).

| Elemental analysis: for C$_{32}$H$_{27}$N$_3$O$_{13}$S | | | |
|---|---|---|---|
| | C | H | N |
| Calculated (%): | 55.40 | 3.92 | 6.06 |
| Found (%): | 54.64 | 4.10 | 4.85 |

IR spectrum (cm$^{-1}$, nujol): 1780, 1740, 1720, 1685, 1670, 1615.

NMR spectrum (δ, DMSO-d$_6$): 2.03 (3H, s), 2.38 (3H, s), 2.44 (3H, s), 3,42 (1H, d, J=18 Hz), 3.52 (1H, d, J=18 Hz), 4.66 (1H, d, J=14 Hz), 4.98 (1H, d, J=14 Hz), 5.04 (1H, d, J=5 Hz), 5.76 (1H, dd, J=8 Hz, 5 Hz), 5.84 (1H, d, J=8 Hz), 7.38–7.50 (5H, m), 7.57 (1H, d, J=8.5 Hz), 8.16 (1H, d, J=8.5 Hz), 9.00 (1H, s), 9.52 (1H, d, J=8 Hz), 10.09 (1H, d, J=8 Hz).

EXAMPLE 5

7β-[D-2-(7,8-Dihydroxychromone-3-carboxamido)-2-phenylacetamido]-3-acetoxymethyl-3-cephem-4-carboxylic acid and its sodium salt (a) 7,8-Dihydroxychromone-3-carbonyl chloride A mixture of 7,8-dihydroxychromone-3-carboxylic acid (6.6 g, 30 mmol) and thionyl chloride (25 ml) was refluxed for 1 hour, and the thionyl chloride was removed. After the addition of benzene to the residue, the mixture was evaporated to dryness and the residue was triturated with n-hexane to give the desired compound (7.2 g).

IR spectrum (cm$^{-1}$, nujol): 1775, 1660, 1620.

(b) 7β-[D-2-(7,8-Dihydroxychromone-3-carboxamido)-2-phenylacetamido]-3-acetoxymethyl-3-cephem-4-carboxylic acid N,O-Bis(trimethylsilyl)acetamide (13.6 ml, 55 mmol) was added dropwise to a stirred suspension of cephaloglycin (4.05 g, 10 mmol) in dichloromethane (100 ml) at 0° C. The mixture was stirred for 1 hour at 0° C., to which was added the acid chloride (2.3 g, 9.5 mmol). After stirring for 1.5 hours at 0° C., the reaction mixture was diluted with ethyl acetate (500 ml), washed successively with saturated brine-1 N hydrochloric acid (1:1, 200 ml×4) and saturated brine (200 ml×6) and dried (MgSO$_4$).

Removal of the solvent afforded solid, to which was added acetone (100 ml). The mixture was stirred at 25° C. overnight and concentrated to a volume of 10 ml. Ethyl acetate and n-hexane were added successively to the residual mixture. The precipitate formed was filtered off and dried to afford the desired compound (1.1 g 18.8%).

Melting point: 235°-250° C. (decomposition).

| Elemental analysis: for $C_{28}H_{23}N_3O_{11}S$ | | |
|---|---|---|
| C | H | N |
| Calculated (%): 55.17 | 3.80 | 6.89 |
| Found (%): 53.21 | 3.47 | 5.45 |

IR spectrum (cm$^{-1}$, nujol): 1780, 1740, 1720, 1660, 1615.

NMR spectrum (δ, DMSO-d$_6$): 2.03 (3H, s), 3.44 (1H, d, J=18 Hz), 3.48 (1H, d, J=18 Hz), 4.68 (1H, d, J=13 Hz), 4.96 (1H, d, J=13 Hz), 5.04 (1H, d, J=5 Hz), 5.76 (1H, m), 5.86 (1H, d, J=8 Hz), 7.08 (1H, d, J=8 Hz), 7.28-7.52 (5H, m), 7.56 (1H, d, J=8 Hz), 8.92 (1H, s), 9.59 (1H, d, J=8 Hz), 10.34 (1H, d, J=8 Hz).

(c) Sodium salt of the compound described in (b)

A suspension of the compound (0.98 g, 1.6 mmol) described in (b) in acetone (200 ml) was filtered and, to the filtrate was added sodium 2-ethyl hexanoate (0.5 M solution in ethyl acetate, 3.04 ml) followed by ethyl acetate-ethyl ether (1:1, 200 ml). The precipitate formed was filtered off, washed with ethyl acetate-ethyl ether (1:1) and dried to afford the desired compound (0.871 g, 85.8%).

Melting point: 230°-240° C. (decomposition).

| Elemental analysis: for $C_{28}H_{22}N_3NaO_{11}S$ | | |
|---|---|---|
| C | H | N |
| Calculated (%): 53.25 | 3.67 | 6.65 |
| Found (%): 49.67 | 3.29 | 5.00 |

IR spectrum (cm$^{-1}$, nujol): 1760, 1660, 1610.

NMR spectrum (δ, DMSO-d$_6$): 2.00 (3H, s), 3.18 (1H, d, J=18 Hz), 3.40 (1H, d, J=18 Hz), 4.64 (1H, d, J=12 Hz), 4.98 (2H, m), 5.60 (1H, m), 5.78 (1H, d, J=8 Hz), 7.04 (1H, d, J=8 Hz), 7.12-7.56 (6H, m), 8.90 (1H, s), 9.40 (1H, br.s), (10.42 (1H, d, J=8 Hz).

The compounds obtained in these examples were tested for their antibacterial activities in vitro.

METHOD

Minimal inhibitory concentration (MIC) was determined by the standard agar dilution method of the Japan Society of Chemotherapy.

The compounds described in Examples 1, 2 and 5 were dissolved in sterilized water; the compound described in Example 4 was dissolved in acetone-water (1:1); and the control compounds, cephaloglycin and cephalexin monohydrate, were dissolved in a 3% sodium hydrogen carbonate solution.

Serial two-fold dilutions were made from the above solutions.

One-ml aliquots of each dilution were mixed with 9 ml of Heart influsion agar in petri-dishes to make agar plates containing the compound at serially diluted concentrations. After agar hardened, plates were put in an incubator at 37° C. for 1.5-2 hours with the lids slightly open to evaporate acetone off the plates.

Test organisms were grown for 18 hours at 37° C. in Trypticase Soy broth and diluted in saline to approximately 10$^6$ colony forming units per ml. A loopful of each cell suspension was applied on the agar plate mentioned above and the plates were incubated for 18 hours at 37° C. before MIC was determined.

MIC values of the compounds described in Examples 1, 2 and 5 were determined as their sodium salts and the compound described in Example 4 was determined as a free carboxylic acid.

The results are shown in Table 2.

TABLE 2

| | MIC (μg/ml) Total bacteria | | | | | |
|---|---|---|---|---|---|---|
| Test compound | Staphylococcus aureus 209P | Escherichia coli NIHJ | Klebsiella pneumoniae EK-6 | Proteus morganii EP-14 | Pseudomonas aeruginosa EP-172 | Serratia marcescens ES-75 |
| Example 1 | 3.13 | 1.56 | ≦0.1 | 50 | 0.8 | 0.4 |
| 2 | 1.56 | 0.8 | ≦0.1 | 12.5 | 0.8 | 0.2 |
| 4 | 1.56 | 0.8 | ≦0.1 | 3.13 | 1.56 | 0.8 |
| 5 | 1.56 | 3.13 | 0.2 | 12.5 | 1.56 | 1.56 |
| Cephaloglycin | 0.8 | 3.13 | 1.56 | 25 | >100 | >100 |
| Cephalexin mono-hydrate | 1.56 | 6.25 | 3.13 | >100 | >100 | >100 |

EXAMPLE 6

A vial was aseptically sealed, so as to involve 125 mg of sodium salt of 7β-[D-2-(6,7-diacetoxychromone-3-carboxamido)-2-phenylacetamido]-3-acetoxymethyl-3-cephem-4-carboxylic acid. In using, 5 ml of distilled water for injection was added thereto, so that injection may be obtained.

EXAMPLE 7

| Tablet | |
|---|---|
| Sodium salt of 7β-[D-2-(6,7-dihydroxy-chromone-3-carboxamido)-2-phenylacetamido]-3-acetoxymethyl-3-cephem-4-carboxylic acid | 250 mg |
| Crystalline cellulose | 80 mg |
| Calcium salt of carboxymethyl cellulose | 38 mg |
| Calcium stearate | 2 mg |
| One tablet | 370 mg |

Tablet was prepared with the above formulation by means of conventional manner.

What is claimed is:

1. A cephalosporin derivative of the formula

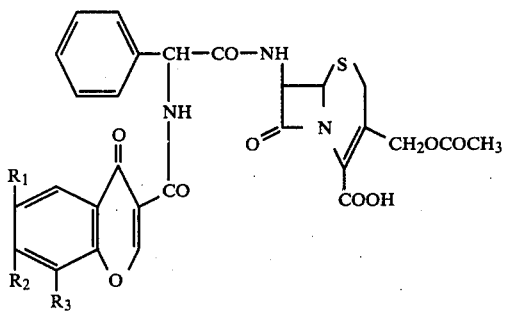

wherein $R_1$, $R_2$ and $R_3$ each represents hydroxy, acetoxy, propionyloxy, or hydrogen, provided that two or three of $R_1$, $R_2$ and $R_3$ are not hydrogen at the same time or a non-toxic salt thereof.

2. A compound according to claim 1 wherein said compound is 7β-[D-2-(6,7-diacetoxychromone-3-carboxamido)-2-phenylacetamido]-3-acetoxymethyl-3-cephem-4-carboxylic acid or non-toxic salt thereof.

3. A compound according to claim 1 wherein said compound is 7β-[D-2-(6,7-dihydroxychromone-3-carboxamido)-2-phenylacetamido]-3-acetoxymethyl-3-cephem-4-carboxylic acid or non-toxic salt thereof.

4. A compound according to claim 1, wherein said compound is 7β-[D-2-(7,8-diacetoxychromone-3-carboxamido)-2-phenylacetamido]-3-acetoxymethyl-3-cephem-4-carboxylic acid or non-toxic salt thereof.

5. The compound according to claim 1, wherein said compound is 7β-[D-2-(7,8-dihydroxychromone-3-carboxamido)-2-phenylacetamidol]-3-acetoxymethyl-3-cephem-4-carboxylic acid or non-toxic salt thereof.

6. An antibacterial composition which comprises an antibacterially effective amount of a cephalosporin derivative of the formula

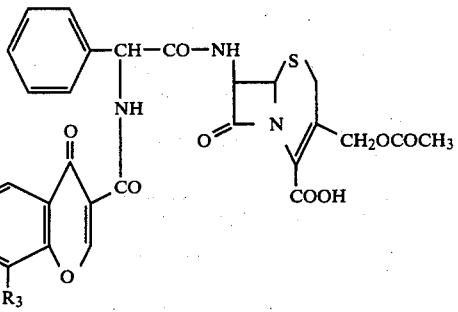

wherein $R_1$, $R_2$ and $R_3$ each represents hydroxy, acetoxy, propionyloxy, or hydrogen provided that two or three of $R_1$, $R_2$ and $R_3$ are not hydrogen at the same time, or a non-toxic salt thereof and a pharmaceutically acceptable carrier therefor.

* * * * *